(12) United States Patent
Graf

(10) Patent No.: US 7,678,085 B2
(45) Date of Patent: Mar. 16, 2010

(54) INJECTION DEVICE

(75) Inventor: Roney Graf, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 1412 days.

(21) Appl. No.: 11/057,398

(22) Filed: Feb. 11, 2005

(65) Prior Publication Data
US 2005/0177116 A1 Aug. 11, 2005

Related U.S. Application Data

(63) Continuation of application No. PCT/CH03/00532, filed on Aug. 7, 2003.

(30) Foreign Application Priority Data
Aug. 14, 2002 (DE) ................................. 102 37 258

(51) Int. Cl.
*A61M 5/00* (2006.01)
(52) U.S. Cl. ................. 604/187; 254/222; 254/233; 254/240; 604/131; 604/134; 604/135; 604/165.01; 604/186; 604/207; 604/208; 604/209; 604/210; 604/211; 604/218; 604/233; 604/234; 604/242
(58) Field of Classification Search ................ 254/222, 254/233, 240; 604/131, 134, 135, 165.01, 604/165.04, 186, 187, 207–211, 218, 233, 604/234, 242
See application file for complete search history.

(56) References Cited
U.S. PATENT DOCUMENTS 4,030,384 A * 6/1977 Newman ................. 81/58.3
4,883,472 A * 11/1989 Michel ..................... 604/208
5,092,842 A * 3/1992 Bechtold et al. .......... 604/135
5,112,317 A * 5/1992 Michel ..................... 604/208
5,114,406 A * 5/1992 Gabriel et al. ............ 604/136
5,207,647 A * 5/1993 Phelps ..................... 604/158
5,304,152 A * 4/1994 Sams ....................... 604/207
5,370,629 A 12/1994 Michel et al.
5,383,865 A * 1/1995 Michel ..................... 604/232
5,480,387 A * 1/1996 Gabriel et al. ............ 604/134

(Continued)

FOREIGN PATENT DOCUMENTS
DE 35 22 459 1/1987

(Continued)

*Primary Examiner*—Nicholas D Lucchesi
*Assistant Examiner*—Scott Medway
(74) *Attorney, Agent, or Firm*—Dorsey & Whitney LLP; David E. Bruhn, Esq.

(57) ABSTRACT

An injection device for injecting selectable amounts of a substance includes an activating mechanism including an axially moveable operating button which can rotated in a resting position only, a tubular drive element non-rotatably connected to the operating button, an axially fixed and non-rotatable guiding element, and an axially moveable driven member held non-rotatably in the device. A rotational grid is operationally between rotatable and non-rotatable components of the injection device such that the operating button can be moved two rotational directions when in the resting position whereby a selected amount of the substance to be injected can be selectively varied. For example, a dosage inadvertently selected too large by rotating the operating button too far in one direction can, in accordance with the present invention, be reduced by rotating the operating button in the opposite direction. In some embodiments, the rotational grid is adapted to produce a clicking sound when the operating button is rotated.

18 Claims, 4 Drawing Sheets

U.S. PATENT DOCUMENTS

| | | | | |
|---|---|---|---|---|
| 5,514,097 A | * | 5/1996 | Knauer | 604/136 |
| 5,593,390 A | * | 1/1997 | Castellano et al. | 604/187 |
| 5,599,314 A | * | 2/1997 | Neill | 604/207 |
| 5,626,566 A | * | 5/1997 | Petersen et al. | 604/208 |
| 5,674,204 A | * | 10/1997 | Chanoch | 604/211 |
| 5,820,602 A | | 10/1998 | Kovelman et al. | |
| 5,827,232 A | | 10/1998 | Chanoch et al. | |
| 5,891,052 A | * | 4/1999 | Simmons | 600/573 |
| 6,086,567 A | * | 7/2000 | Kirchhofer et al. | 604/211 |
| 6,090,080 A | * | 7/2000 | Jost et al. | 604/207 |
| 2003/0160072 A1 | | 8/2003 | Geiser et al. | |

FOREIGN PATENT DOCUMENTS

| | | |
|---|---|---|
| EP | 0 581 924 B1 | 2/1994 |
| WO | WO 87/02895 | 5/1987 |
| WO | WO 93/16740 | 9/1993 |
| WO | WO 01/72361 A1 | 10/2001 |
| WO | WO 01/95959 A1 | 12/2001 |
| WO | WO 02/24260 A1 | 3/2002 |
| WO | WO 02/092153 A2 | 11/2002 |

* cited by examiner

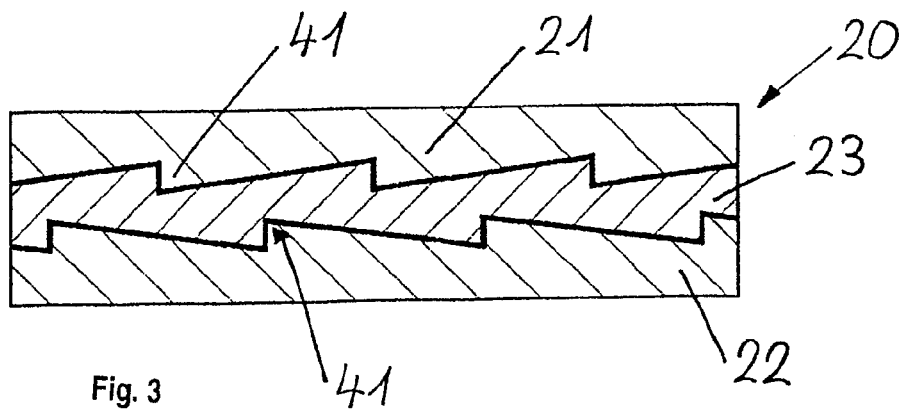
Fig. 3
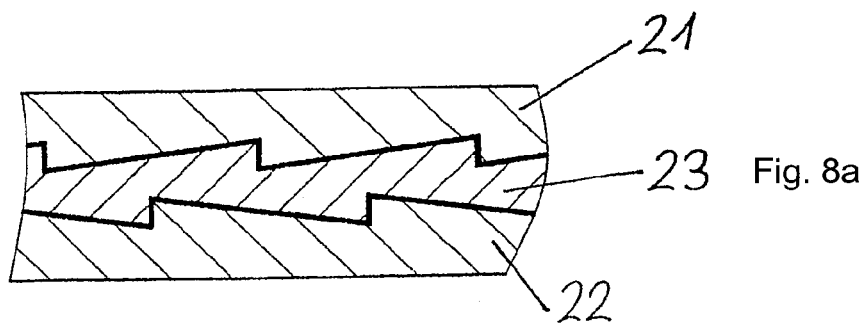
Fig. 8a
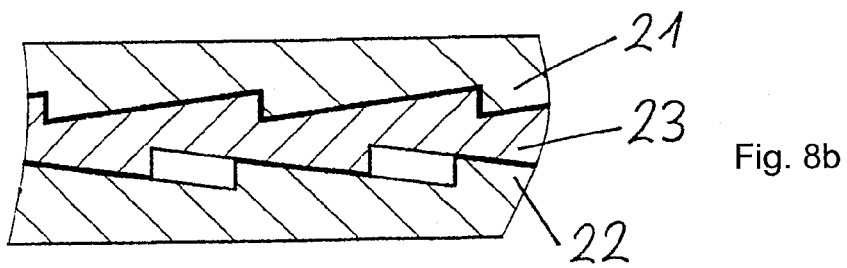
Fig. 8b
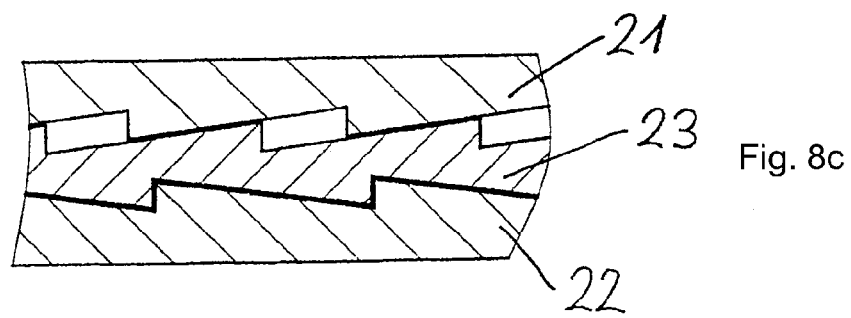
Fig. 8c
Fig. 8

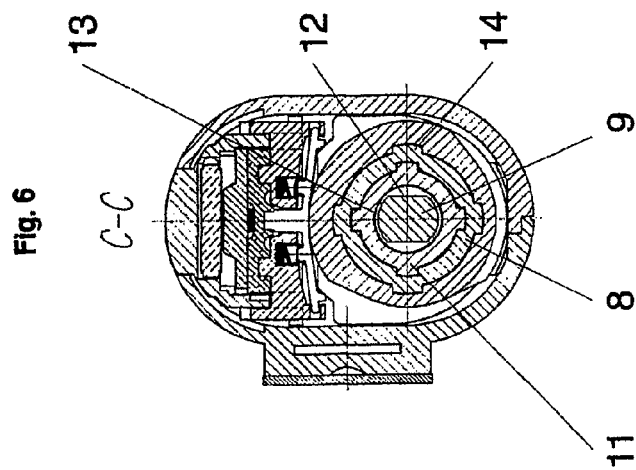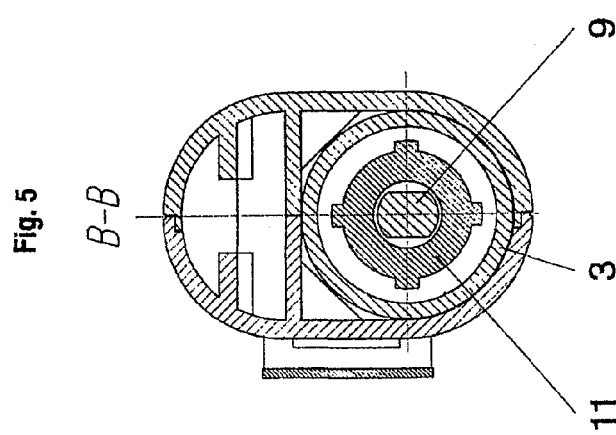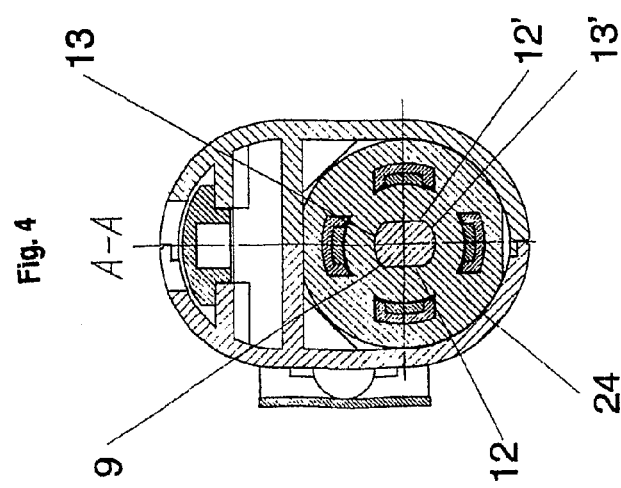

INJECTION DEVICE

CROSS-REFERENCE TO RELATED APPLICATION(S)

This application is a continuation of International Application No. PCT/CH2003/00532, filed Aug. 7, 2003, which claims priority to German Application No. 1 0237258.6, filed on Aug. 14, 2002, the contents of which is incorporated in their entirety by reference herein.

BACKGROUND

The present invention relates to devices and methods for administering or delivering substances, including injection devices and methods for making and using them. More particularly, it relates to an injection device for administering an injectable product, in doses, from a product container or ampoule provided with a piston.

In one embodiment, the injection device comprises a generally tubular activating means which can be driven manually, an operating button on which axial movements and rotational movements can be performed, a drive element which is non-rotatably connected to the operating button and follows the movements of the operating button, and a driven member, operably coupled to the drive element, which can be moved in the advancing direction of the piston, wherein when the operating button is moved axially, the drive element can be shifted in the advancing direction of the piston from a resting position to an end position and back again, this movement transferable onto the driven member.

An injection device of the type suitable for the present invention is known from EP 0 581 924 B1 (belonging to the Applicant), the disclosure and teachings of which are incorporated herein by reference. The known injection device serves to inject respectively selectable amounts of a liquid product, which preferably contains a medical or therapeutic active agent, from a product container provided with a piston, in particular from an ampoule. The device comprises a tubular activating means which can be driven manually and which comprises an operating button which can be axially and rotationally moved, a drive element which is non-rotatably connected to the operating button and follows the movements of the operating button, a driven member which is non-rotatable with respect to a casing of the device, and a guiding element for the driven member.

In the known device, a drive element—on which the driven member is movably mounted—can be shifted axially, i.e. in the advancing or dispensing direction of the piston, by a distance predefined by the mechanism, from a resting position to a front end position. The product dosage to be delivered is set by rotating the operating button.

In one embodiment, a rotational grid is provided between non-rotatable and rotatable parts of the known injection device and comprises two discoid locking elements which oppose each other and each comprise a plurality of locking protrusions and a plurality of locking recesses preferably corresponding to or complementing the locking protrusions, and which co-operate with each other.

When the dosage to be injected is set by rotating the operating button, the locking protrusions slide off on the locking recesses, producing a sound which is uniquely dependent on the rotational movement of the operating button. In the device of EP 0 581 924 B1, a clicking sound is produced every time the locking protrusions resile into the locking recesses formed to correspond to them. By counting out on the basis of the sound produced, in particular on the basis of the number of clicking sounds, the patient can set the quantity of the new injection dosage purely aurally, i.e., without looking at the device. Setting the dosage to be injected aurally in this way has proven very advantageous, in particular for patients who have developed impaired vision due to an illness, as is, for example, often the case with diabetes patients.

In the prior art, the rotational grid consists of two disc-shaped locking elements on which serrated locking protrusions or locking recesses, respectively, are arranged at regular intervals in the circumferential direction. The two locking elements are pressed against each other by means of a spring serving as a restoring element, such that the rotational grid and/or operating button can only be rotated in one rotational direction and are blocked in the other rotational direction. This has the disadvantage that a dosage which has been set by rotating the operating button in the first rotational direction can only then be increased further, i.e., by rotating the operating button further in the first direction, but cannot be reduced by rotating the operating button back in the opposite rotational direction. Thus, if the patient has inadvertently selected too large a dosage, for instance because he has incorrectly counted the number of clicking sounds, then the incorrectly selected dosage must first be delivered by advancing the driven member to the front end position. The driven member must then be moved back to the resting position before a new dosage can be set. This procedure is tedious, fraught with error and unnecessarily wastes a lot of product.

SUMMARY

It is an object of the present invention to provide an injection device wherein the dosage to be administered can be simply and reliably pre-set, and wherein it is also possible at any time to reduce a dosage which has once been set.

In one embodiment, the present invention comprises an injection device for injecting selectable amounts of a substance includes an activating mechanism including an axially moveable operating button which can rotated in a resting position only, a tubular drive element non-rotatably connected to the operating button, an axially fixed and non-rotatable guiding element, and an axially moveable driven member held non-rotatably in the device, wherein a rotational grid is operationally between rotatable and non-rotatable components of the injection device such that the operating button can be moved two rotational directions when in the resting position whereby a selected amount of the substance to be injected can be selectively varied. For example, a dosage inadvertently selected too large by rotating the operating button too far in one direction can, in accordance with the present invention, be reduced by rotating the operating button in the opposite direction. In some embodiments, the rotational grid is adapted to produce a clicking sound when the operating button is rotated.

The present invention relates to an injection device for injecting respectively selectable amounts of liquid, preferably insulin, from an ampoule. A manual activating means comprises: an operating button which can be axially moved, and rotated in a (rear) resting position only; a tubular drive element which is non-rotatably connected to the operating button; an axially fixed and non-rotatable guiding element; and a driven member which can be axially moved, is held non-rotatably in the device and advances the piston of the ampoule. A rotational grid is provided between rotatable and non-rotatable parts of the injection device and, when the operating button is rotated, produces acoustic sounds, for example clicking sounds, in accordance with the dosage set. In accordance with the invention, the rotational grid is configured such that the operating button can be moved in both rotational directions in its (rear) resting position. A dosage which has inadvertently been selected too large by rotating the operating button too far in a rotational direction can, in accordance with the invention, be reduced again by simply rotating the operating button back in the opposite rotational direction, wherein audible acoustic sounds can also be produced when rotating the operating button back, on the basis of which the patient can determine the set dosage aurally.

An injection device in accordance with the invention is characterised in that the rotational grid is configured such that the operating button can be moved in both rotational directions in its resting position, i.e., when the driven member is spaced apart from the piston. Because the device in accordance with embodiments of the present invention comprises a rotational grid which emits acoustic sounds—preferably, clicking sounds—when rotated, the patient can also continue to pre-set the dosage audibly or aurally, in particular on the basis of counting the number of clicking sounds. This ensures that dosing is simple and reliable. Because, in accordance with the invention, the rotational grid can be moved in both rotational directions in the resting position, the dosage which has been selected once can also simply be reduced again, without delivering the product unnecessarily, as explained above.

Preferably, the rotational grid produces the aforesaid acoustic clicking sound not only when the operating button is rotated in the first rotational direction, for example clockwise, but also when the operating button is rotated in the opposite rotational direction, for example anti-clockwise. Thus, the patient can also orientate himself on the basis of the produced acoustic sound and deduce the respectively set dosage when rotating the operating button and/or rotational grid back. The injection device in accordance with the invention can therefore be simply and reliably operated, even without being read.

In accordance with a preferred embodiment, the operating button and together with it the driven member can only be axially adjusted from the resting position to the front end position when the rotational grid is locked in and the locking protrusions are co-operating substantially completely with the locking recesses formed to correspond to and/or complement them. In this simple way, it is possible to ensure that only a dosage which is set by rotating the operating button by an integer multiple of the circumferential angular intervals of the locking protrusions can be administered.

In the aforesaid embodiment, a number of locking bodies, for example recesses running in the axial direction and correspondingly formed protrusions running in the axial direction, are preferably formed on the outer circumference of the operating button or on an element arranged non-rotatably with respect to it, wherein the number of locking bodies preferably corresponds to the number of locking protrusions formed on the facing sides of the locking elements of the rotational grid. Only when the locking bodies permit the operating button and the driven member coupled to it to advance axially can the set dosage actually be administered.

In some preferred embodiments, the aforesaid locking bodies also produce an acoustic sound, in particular clicking sounds, which are preferably produced synchronously with the acoustic sounds, in particular the clicking sounds, of the rotational grid, such that the angular positions of the locking bodies preferably correspond substantially to the angular positions of the locking protrusions and/or recesses of the rotational grid.

In accordance with a preferred embodiment, a second restoring element is provided which axially retracts an ampoule holder—which forms a first locking element, for example a lower disc, of the rotational grid or is coupled to it—towards the operating button, such that the rotational grid locks in, wherein in the locked-in position of the rotational grid, the locking protrusions co-operate substantially completely with the locking recesses formed to correspond to them, engaging substantially completely with them. The second restorer can, for example, be between the rear part of the injection device, where the activating means which can be manually driven sits, and the ampoule holder.

In some preferred embodiments, the restoring force of the second restoring element is smaller than that of the first restoring element, such that the rotational grid is not mounted rigidly, but rather sprung, such that the locking elements of the rotational grid, abutted against each other by the restoring elements, elastically resile when the locking protrusions slide off on the locking recesses, which makes the acoustic sound produced even more audible.

The present invention can be applied to devices of the type described in EP 0 581 924 B1, although it is not in principle restricted to the specific embodiment described in EP 0 581 924 B1. In such an embodiment, a drive element—on which the driven member is movably mounted—can be shifted axially, i.e. in the advancing direction of the piston, by a distance predefined by the mechanism, from a resting position to a front end position. Over a part of the predefined distance, the driven member does not abut the piston of the product container. Over the remaining part of the predefined distance, the driven member abuts the piston stopper, such that when the driven member is advanced further by the remaining part of the predefined distance, the piston is axially advanced, such that a product, such as a medicinal substance or liquid, is delivered from the product container. Once the product has been delivered, the driven member is returned to the resting position with the aid of a restorer. If the driven member were again advanced axially by the distance set for the previous injection, no further product would be delivered from the product container because the driven member is not able to abut the piston.

In some embodiments, the product is dosed as in the following steps. In its resting position, the operating button can moved rotationally. When the operating button is rotated in the resting position, for example clockwise, the driven member—which is not then abutting the piston—is axially advanced in a controlled way, shortening the interval between the driven member and the piston. The distance by which the interval between the driven member and the piston is shortened when the operating button is rotated corresponds to the distance during which the driven member abuts the piston as it is advanced to the front end position, in order to deliver another product dosage from the product container. The rotational angle by which the operating button is rotated in the first direction, for example clockwise, thus unequivocally defines the product dosage to be delivered.

In one embodiment, the present invention comprises a method of injecting a selectable amount of a substance, comprising the steps of providing an injection device comprising an activating mechanism comprising an axially moveable operating button which can rotated in a resting position only, a tubular drive element non-rotatably connected to the operating button, an axially fixed and non-rotatable guiding element, an axially moveable driven member held non-rotatably in the device, and a rotational grid operationally between rotatable and non-rotatable components of the injection device such that the operating button can be moved two rotational directions when in the resting position, and rotating the operating button to select an amount of the substance to be injected, wherein if too large an amount is inadvertently selected by rotating the operating button too far in one direction, the too large an amount can be reduced by rotating the operating button in the opposite direction. In some embodiments, the rotational grid is adapted to produce a sound when the operating button is rotated, the method further comprising assessing the amount selected by listening to the sound.

BRIEF DESCRIPTION OF THE DRAWINGS

FIG. 3 schematically shows another embodiment of a rotational grid in accordance with the invention, in a developed view;

FIG. 4 is a cross-section along line A-A of FIG. 1;

FIG. 5 is a cross-section along line B-B of the injection device in accordance with FIG. 1;

FIG. 6 is a cross-section along line C-C of the injection device in accordance with FIG. 1;

FIG. 8, including FIGS. 8a-8c, depicts three different angular positions of an operating button of an injection device in accordance with the invention.

DETAILED DESCRIPTION

Figure 1:
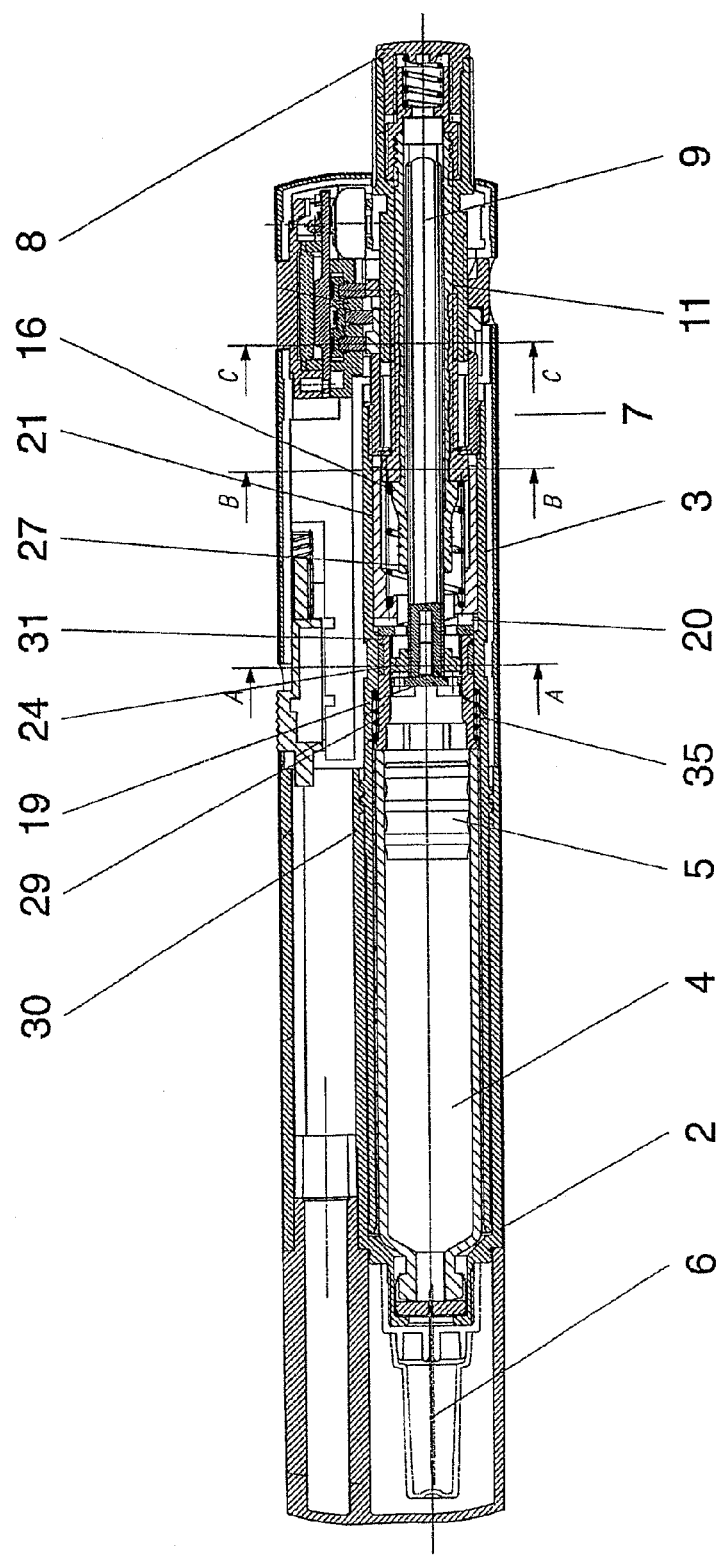
FIG. 1 is a longitudinal section through an injection device of the type which is suitable for use in the present invention.

In the figures, identical reference numerals indicate identical or substantially functionally identical elements and functional groups.

In order to better illustrate the functionality of an injection device in accordance with the invention, an injection device is shown in a longitudinal section in FIG. 1. This type of device may be understood by reference to FIG. 2 of EP 0 581 924 B1, belonging to the Applicant. The present invention is not, however, restricted to this specific embodiment of an injection device.

Referring then to FIG. 1, a front part 2 of the injection device comprises an exchangeable ampoule 4 in which a piston 5 sits such that it can be axially adjusted, said piston 5 delivering the substance stored in the ampoule, which preferably contains a medical or therapeutic active agent, through an injection needle 6. The rear part 3 of the device has an activating means 7, designed in the shape of a tube, which can be operated by hand. The activating means 7 comprises an operating button 8, a driven member formed substantially as a rod 9 with a flange 19, a guiding element 24 and a drive element 11.

As shown in the cross-sections in accordance with FIGS. 4-6, the rod 9 has plane surfaces on both sides and otherwise exhibits a circular cross-section which bears a thread. This thread sits in a female thread 27 of the drive element 11, which sits non-rotatably in the injection device. The drive element 11 can be transferred, together with the entire activating means 7, from a (rear) resting position to a (front) end position by axially activating the operating button 8 and conveying this movement via the guiding element 24, against the force of a spring 16 serving as a first restorer. The rod 9 participates in this axial advancing movement, wherein the flange 19 situated on the rod 9 eventually presses against the piston 5 of the ampoule 4, pushes it forwards and thus effects the injection.

The rod 9 sits non-rotatably, but can be moved axially, in the guiding element 24. The guiding element 24 for its part is connected non-rotatably to the operating button 8. As shown in the cross-section in accordance with FIG. 4, the guiding element 24 has an inner contour which (except for any suitable tolerances) is adapted to the outer contour of the rod 9 as described above. The operating button 8, the guiding element 24 and the rod 9 can only be rotated in the (rear) resting position of the activating means 7. The rod 9 then rotates in the female thread 27 of the drive element 11 arranged non-rotatably in the injection device, and is this adjusted forwards when the operating button 8 is rotated in a first rotational direction, for example clockwise. As will also be explained below, the operating button in accordance with the prior art cannot be rotated back in the opposite direction—i.e. in the aforesaid case, anti-clockwise—in the state shown in FIG. 1.

As described above, a substance is injected by axially advancing the operating button and the flange 19 serving as the driven member towards the front end position, wherein the operating button and therefore the flange 19 can each be advanced by a unitary, predefined distance only, which is, for example, pre-set by stoppers in the activating means 7 and by the maximum stroke of the operating button 8. If, after an injection, the operating button 8 is guided back to the (rear) resting position, then no further substance would be delivered from the ampoule 4 if the operating button 8 and the flange 19 were again advanced axially. In order to deliver a subsequent, new dosage, the flange 19 has to be advanced by a distance corresponding to the dosage to be administered, by rotating the operating button 8 in the first rotational direction, such that the distance between the flange 19 serving as the driven member and the piston 5 is shortened by said pre-settable distance. Thus, when the operating button 8 and the flange 19 serving as the driven member are again advanced, the flange 19 abuts the piston 5 at the end of its axial advancing movement and shifts it axially forwards by the distance set by the rotational movement of the operating button 8, such that a new dosage is delivered from the ampoule 4 which is substantially unequivocally defined by the rotation of the operating button 8.

The tubular drive element 11 is connected to the operating button 8, fixed against rotating. The operating button 8, which can be axially moved, can only be rotationally moved in its (rear) resting position, and—in accordance with EP 0 581 924 B1—only in one rotational direction, in order to axially advance the flange 19 serving as the driven member. The rod 9, whose threaded parts on the circular surfaces 13, 13' engage with the female thread 27 of the drive element 11, is held in the interior of the drive element 11. The rod 9 penetrates through the drive element 11 and the guiding element 24. The latter is fixedly connected to the rear part 3 of the injection device and can move neither axially nor rotationally. The opening in the guiding element 24, adapted to the rod 9, ensures that the rod 9 can only move axially and not rotationally.

If the operating button 8 is manually advanced axially, it shifts the drive element 11 as far as its (front) end position, which is defined by a stopper 31, for example a stopper of the drive element 11 on the guiding element 24. This axial movement is transferred onto the rod 9 sitting in the female thread 27 of the drive element 11, the rod 9 only being able to move axially and not rotationally.

The axial movement is performed against the force of a spring 16 which serves as a first restorer and sits in a cavity between the drive element 11 performing the axial movement and a sleeve part 21 of the rotational grid 20 to be described below. The spring 16 urges and moves the activating means 7 back to its resting position again.

Because the rod 9 is mounted non-rotatably in the guiding element 24, the rotational movement exerted on the operating button 8 in order to set the next injection dosage cannot be transferred onto the rod 9. Rather, the rod 9 is non-rotatably driven axially forwards by the rotating female thread 27 of the drive element 11, via the threaded parts on the circular surfaces 13, 13' (cf. FIG. 4), and so moves the flange 19 to the position corresponding to the next injection dosage to be dispensed. When the flange 19 is axially advanced, the distance between the flange 19 and the piston 5 is reduced in accordance with the rotation of the operating button 8.

The flange's 19 path from the (rear) resting position to the (front) end position of the activating means 7 remains constantly the same and corresponds to the constant distance by which the flange 19 is separated from the piston 5 before the injection dosage is set. Thus, by rotating the operating button 8 in the (rear) resting position, the injection dosage to be administered can be set in advance. By rotating the operating button 8 in the first rotational direction in a controlled way, the injection dosage can thus be substantially unequivocally defined.

In order that the injection dosage can also be reliably set aurally or audibly, on the basis of acoustic sounds, a two-part rotational grid is known from the generic EP 0 581 924 B1 which only permits the operating button 8 to rotate in the first rotational direction, for example clockwise, and blocks it from rotating in the second, opposite rotational direction, for example anti-clockwise. When the rotational grid is rotated, locking protrusions slide off on locking recesses, such that a defined acoustic sound, e.g. a clicking sound, is produced in unique correlation with the rotational movement of the operating button 8.

Figure 7:
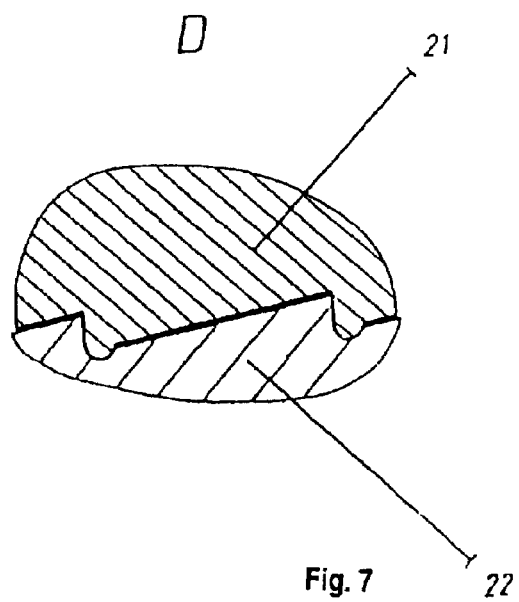
FIG. 7 shows details of a two locking element rotational grid.

The rotational grid 20 sits generally between the non-rotatable and rotatable parts of the injection device. The rotational grid 20 is schematically shown in FIG. 7. In accordance with EP 0 581 924 B1, the rotational grid 20 comprises two locking elements 21, 22 which abut each other in the aforesaid resting position and comprise a plurality of serrated locking protrusions, and/or locking recesses formed to correspond to the protrusions, running in the circumferential direction and preferably arranged at regular angular intervals, as shown in FIG. 7. The locking element 22 corresponds to the ampoule holder 29 or is mechanically coupled to it. The locking element 21 corresponds to a sleeve part of the tubular drive element 11 which is rotatably mounted and non-rotatably connected to the operating button 8.

When the two locking elements 21, 22 are rotated relative to each other, the serrated locking protrusions slide off on the correspondingly formed and/or complementary locking recesses. Because the two locking elements 21, 22 are pressed against each other by means of the restoring force of the spring 16 serving as a first restorer, the two locking elements 21, 22 resile after completely sliding off a serrated locking protrusion, which produces a clearly audible clicking sound which serves as an acoustic sound for setting the injection dosage "aurally". The rotational grid in accordance with EP 0 581 924 B1—and, correspondingly, as set forth in WO 87/02895—can only be moved rotationally in one rotational direction. Thus, if the operating button 8 is rotated too far in the first rotational direction, for instance because a user has incorrectly counted the number of clocking sounds, then the operating button 8 cannot be rotated back. The incorrectly set injection dosage cannot therefore be reduced again. Rather, the substance has to be unnecessarily delivered by axially advancing the operating button 8 and a new injection dosage cannot be reset until the operating button 8 has returned to the (rear) resting position.

Figure 2:
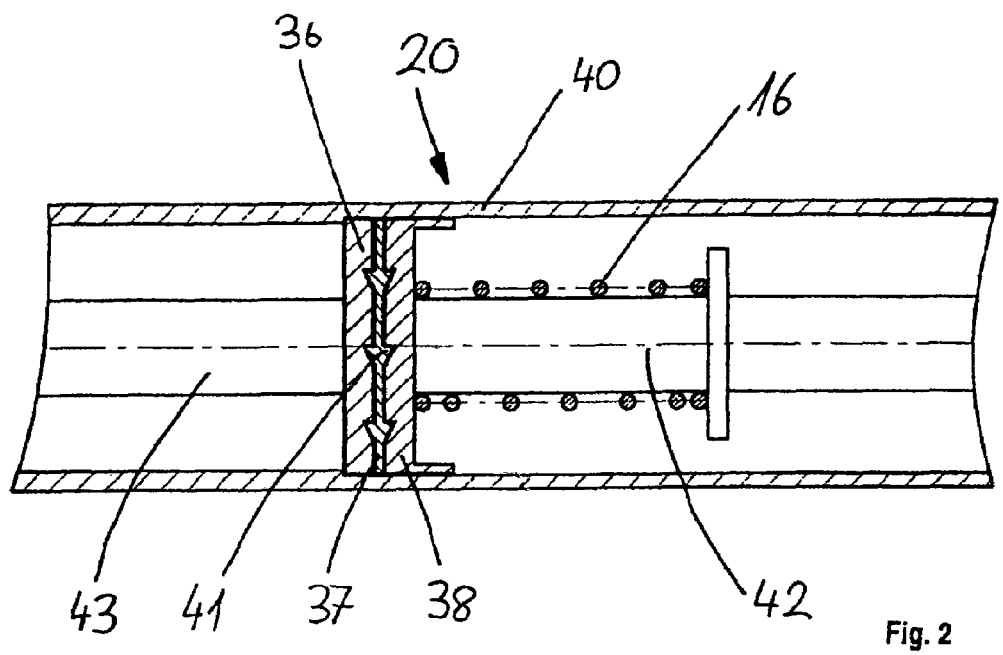
FIG. 2 schematically shows a rotational grid in a longitudinal section, in accordance with an embodiment of the present invention.

In accordance with the present invention, the rotational grid 20 comprises more than two locking elements which can be rotated relative to each other, in some embodiments, three locking elements which can be rotated relative to each other. FIGS. 2 and 3 schematically show two exemplary embodiments of the present invention.

FIG. 2 shows a partial longitudinal section of a first exemplary embodiment in which the rotational grid 20 comprises a lower sliding sleeve 36, a sagittal ring 37 comprising locking protrusions 41 and serving as an intermediate disc and an upper sliding sleeve 38. The upper sliding sleeve 38 is non-rotatably connected to the operating button 8 (not shown in FIG. 2), for example via the schematically shown cylindrical intermediate piece 42. The lower sliding sleeve 36 is preferably connected to the ampoule holder 29, for example via the schematically shown cylindrical intermediate piece 43.

The disc-shaped sliding sleeves 36, 38 serving as locking elements and the sagittal ring 37 comprise a plurality of locking protrusions 41 and locking recesses formed to correspond to and/or complement the protrusions.

If the upper sliding sleeve 38 is rotated to the left, then the locking recesses formed in it slide off on the locking protrusions 41, resulting in their being axially retracted against the restoring force of the spring 16. If the upper sliding sleeve 38 is rotated further to the left, the locking recess eventually engages with the next locking protrusion 41. Due to the restoring force of the spring 16, the upper sliding sleeve 38 resiles and thereby produces an audible clicking sound. Due to the corresponding PF separation of the locking protrusions 41 on the sagittal ring 37, it is blocked to the left when the upper sliding sleeve 38 is rotated, thus remaining in the locking recesses formed on the facing side of the upper sliding sleeve 38.

If, by contrast, the operating button 8 (not shown) is rotated to the right in FIG. 2, i.e. in the opposite rotational direction, then the locking protrusions 41 on the upper facing side of the sagittal ring 37 and the locking recesses formed on the facing side of the upper sliding sleeve 38 remain hooked to each other, and the locking recesses formed on the lower facing side of the sagittal ring 37 slide off on the locking protrusions formed on the upper facing side of the lower sliding sleeve 36. This axially retracts the sagittal ring 37 and the upper sliding sleeve 38, against the restoring force of the spring 16. If the operating button 8 is rotated further to the right, the locking protrusions formed on the lower facing side of the sagittal ring 37 eventually engage with the next locking recess on the upper facing side of the lower sliding sleeve 36, wherein the upper sliding sleeves 38 and the sagittal ring 37 resile due to the restoring force of the spring 16, producing a clearly perceptible clicking sound.

In accordance with the invention, therefore, clicking sounds or suitable, generally comparable acoustic sounds are produced when the operating button 8 is rotated both clockwise and anti-clockwise. The patient thus only has to note in which direction he or she is turning the operating button 8 and can thus deduce or assess the set or selected injection dosage from the number of clicking sounds. If an inadvertently too large an injection dosage has been set by rotating the operating button 8 in the first rotational direction, for example clockwise, then in accordance with the invention, the user can rotate the operating button 8 in the opposite rotational direction, i.e. in reverse, for example, anti-clockwise, and reduce the injection dosage again. Clicking sounds or comparable acoustic sounds are also produced when the operating button 8 is rotated back, from which the user can deduce the injection dosage.

In the exemplary embodiment in accordance with FIG. 2, the locking protrusions 41 provided on mutually opposing facing sides of the sagittal ring 37 serving as the intermediate disc are arranged—as viewed in the advancing direction of the piston 5—at mutually flush angular positions.

FIG. 3 shows another exemplary embodiment in accordance with the present invention, in which locking protrusions on an upper and lower disc, each serving as a locking element, are arranged—as viewed in the advancing direction of the piston 5—at angular positions offset with respect to each other, in the resting position of the operating button 8. In accordance with FIG. 3, the rotational grid 20 comprises an upper disc 21, a lower disc 22 and an intermediate disc 23. The upper disc 21 and the lower disc 22 comprise a plurality of serrated locking protrusions 41, in some preferred embodiments, arranged at regular angular intervals. Corresponding to or complementing these, the intermediate disc 23 also comprises locking protrusions and locking recesses. The upper disc 21 pressed towards the lower disc 22 by the restoring force of a spring 16 (not shown in FIG. 3) serving as a first restorer. In the resting position of the operating button 8, the locking protrusions 41 preferably engage substantially completely with the locking recesses formed to correspond to them.

When the upper disc 21 is rotated relative to the lower disc 22, the result is the progression of movement shown schematically in the views in accordance with FIG. 8, including FIGS. 8*a*-8*c*. FIG. 8*a* shows the initial state of the rotational grid 20 in the resting position of the operating button 8 (not shown), in which the overall height of the rotational grid 20 is at a minimum. When the upper disc 21—which is non-rotatably connected to the operating button 8 (not shown in this Figure)—is rotated to the left, the locking protrusions formed on the upper facing side of the intermediate disc 23 remain hooked to the locking recesses formed on the lower facing side of the upper disc 21, such that the locking protrusions formed on the lower facing side of the intermediate disc 23 slide off on the locking recesses, formed to correspond to them, on the upper facing side of the lower disc 22. When rotated further, the locking protrusions formed on the lower facing side of the intermediate disc 23 eventually reach the next locking protrusions. Due to a restoring force, the discs 21, 22, 23 are then pressed onto each other, such that the initial position of the rotational grid 20 shown in FIG. 8*a* is again assumed. When the upper disc 21 and intermediate disc 23 resile, a perceptible clicking sound is produced.

When the upper disc 21 is rotated in the opposite rotational direction, i.e. to the right in FIG. 8*c*, the result is a corresponding progression of movement which can be directly gathered from FIG. 8*c*.

The various locking elements of the rotational grid 20, i.e. the discs 36 to 38 in the exemplary embodiment in accordance with FIG. 2 and the discs 21 to 23 of the second exemplary embodiment in accordance with FIG. 3, respectively, are reset and abutted against each other with the aid of two restorers, preferably springs, as follows. As shown in FIG. 1, the front part 2 is connected to the rear part 3 of the injection device via the coarse thread 30. While the tubular drive element 11 sits in the rear part 3, the ampoule 4 sits in the front part 2 of the injection device. An ampoule holder 29, which is, in some embodiments, in the shape of a hollow cylinder and through which the flange 19 serving as the driven member penetrates, lies on the upper facing edge of the ampoule 4. In order to elastically mount the ampoule 4 in the front part 2 of the injection device, a spring 35 serving as the second restorer sits between the ampoule holder 29 and the rear part 3. If the ampoule 4 is sitting loosely on the ampoule holder 29, for instance because the front part 2 is not yet completely screwed onto the coarse thread 30, then the second spring 35 pushes the ampoule 4 and the ampoule holder 29 axially forwards. Because one side of the rotational grid 20 in accordance with the invention, for example the lower disc 36 in FIG. 2 or the lower disc 22 in FIG. 3, is coupled to or formed by the ampoule holder 29, the rotational grid 20 thus disengages. In this position, the operating button 8 can be rotated back without locking resistances, for example in order to fully return the flange 19 and the rod 9 to an initial position when a new ampoule 4 is to be inserted, the piston 5 of which is initially in the rearmost end position.

The length of the ampoule 4 and the length of a receptacle serving to store the ampoule 4 in the front part 2 are adjusted to each other, such that when the front part 2 is completely screwed onto the coarse thread 30, the rotational grid in accordance with the invention fully locks in, i.e. assumes an initial position in which the complementary locking protrusions and locking recesses engage substantially completely and full-face with each other, as shown for example in FIG. 2, FIG. 3 and FIG. 8*a*.

In this initial position, the second spring 35 is preferably not fully compressed, such that when the rotational grid 20 in accordance with the invention is rotated, the progressions of movement of the locking elements of the rotational grid 20—described above on the basis of FIGS. 2, 3 and 8—can be performed, in order to produce acoustic sounds, preferably clicking sounds.

The operating button 8 for delivering the dosage set can preferably only be axially shifted from the (rear) resting position to the (front) end position when the rotational grid 20 is locked in, i.e. when it assumes the initial position shown in FIG. 2 and in FIGS. 3 and 8*a*, respectively, in which the locking protrusions and the locking recesses engage substantially completely and full-face with each other. This measure ensures that the dosings which may be administered cannot be set across a continuum, but only in integer multiples of minimum dosages which are substantially unequivocally preset by the angular distance of the locking protrusions of the rotational grid 20. This simultaneously ensures that when the rotational grid 20 is rotated by one locking protrusion, corresponding to increasing or reducing the dosage set by a minimum dosage, a clicking sound or comparable acoustic sound is produced. In accordance with this preferred embodiment, the operating button 8 can only be axially shifted when—after the aforesaid resiling and the clicking sound thus produced—the rotational grid 20 again assumes the initial position shown in FIGS. 2, 3 and 8*a*, respectively.

For this purpose, a number of locking bodies can be arranged on the outer circumference of the operating button 8 or on an element—for example, a guiding sleeve—arranged non-rotatably with respect to it, wherein the number of locking bodies corresponds to the number of locking protrusions on the facing sides of the locking elements 21-23 and 36-38, respectively, of the rotational grid 20 in accordance with the invention. As shown schematically in FIG. 6, which is a cross-section along line C-C in FIG. 1, the operating button 8 bears four locking bodies 14 on its outer circumference in this example, which are arranged at equal angular intervals, i.e. at 90°, and are formed as axially running protrusions, wherein FIG. 6 is based on the non-restricting assumption that the rotational grid respectively comprises four locking protrusions and/or locking recesses on the facing sides of the locking elements. In their angular position with respect to the locking protrusions and/or locking recesses on the respective facing sides of the rotational grid 20 in accordance with the invention, the locking bodies 14 can be arranged flush or offset. Only when an axial groove, formed in the ring surrounding the operating button 8 to correspond to the locking body 14, is flush can the operating button 8 be axially shifted.

This angular position is preferably co-ordinated with the angular position in which the rotational grid 20 is locked in.

In the injection device-shown in FIG. 1, the fixed guiding element 24 lies in front of the tubular drive element 11. The drive element 11, installed non-rotatably in the injection device 1, can of course also be arranged in front of the guiding element 24 in accordance with the present invention, said arrangement being known, for example, from WO 87/02895. Instead of the cylindrical ampoule 4 shown in the figures, a different vessel comprising a piston 5 can also be used as the product container.

While a specific embodiment has been described above, similar to the injection device known from EP 0 581 924 B1 belonging to the Applicant, the present invention is not in principle restricted to this specific embodiment. Rather, the present invention can in principle be applied to comparable injection devices in which a rotational grid or comparable latching block is provided between non-rotatable and rotatable parts of the device. An example of another such embodiment is known from WO 97/17096 belonging to the Applicant. This document is expressly to be incorporated by the present application by way of reference. In an injection device comparable to WO 97/17096, the dosage is set by rotating an operating button. When the operating button is rotated, a threaded nut is shifted along a thread, altering the distance between the threaded nut and the piston of the ampoule. When the operating button is axially activated, the threaded rod and the piston are axially adjusted by the distance pre-set in this way, in order to deliver the product in doses.

The injection device in accordance with the invention may be preferably used in auto-therapy by diabetes patients in which they self-administer insulin doses prescribed by their doctor. For this purpose, in some embodiments, the injection device preferably comprises a 30-gauge or 31-gauge injection needle 6.

In the foregoing description, preferred embodiments of the invention have been presented for the purpose of illustration and description. They are not intended to be exhaustive or to limit the invention to the precise forms or steps disclosed. Obvious modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for administering an injectable product, in doses, from a product container provided with a piston, said injection device comprising:

activating means which can be driven manually and comprising: an operating button on which axial movements and rotational movements can be performed; a drive element non-rotatably connected to the operating button and which follows the movements of the operating button; and a driven member which can be moved in an advancing direction of the piston, wherein, when the operating button is moved axially, the drive element can be shifted in the advancing direction of the piston from a resting position to an end position and back again and this movement can be transferred onto the driven member connected to the drive element; and a rotational grid generally between non-rotatable and rotatable parts of the device and comprising at least two mutually opposing locking elements having a plurality of co-operating locking protrusions and locking recesses, wherein the locking elements are abutted against each other by a first and a second restorer situated on opposite sides of the locking elements and, when the operating button is rotated in the resting position, the locking protrusions slide relative to the locking recesses producing a sound, and wherein the rotational grid is configured such that the operating button can be moved in two rotational directions in the resting position;

wherein the operating button can only be moved axially to the end position when the rotational grid is locked in the resting position, wherein a number of locking bodies provided on the operating button or an element arranged non-rotatably with respect to the operating button are arranged such that the locking bodies are movable from an offset position to a flush position relative the locking protrusions or recesses of a facing side of the rotational grid, and when the locking bodies are in the offset position, the rotational grid is unlocked and the operating button is not axially movable to the end position, and when the locking bodies are in the flush position, the rotational grid is locked in the resting position such that the operating button is axially movable.

2. The injection device as set forth in claim 1, wherein the rotational grid comprises an upper and a lower disc and an intermediate disc arranged generally between them which respectively comprises, on its facing sides, at least one of locking protrusions and locking recesses respectively corresponding to the locking protrusions and locking recesses on the respective discs.

3. The injection device as set forth in claim 2, wherein the locking protrusions are formed as serrated protrusions running in the circumferential direction of the discs.

4. The injection device as set forth in claim 2, wherein the locking protrusions on mutually opposing sides of the intermediate disc are arranged at mutually flush angular positions.

5. The injection device as set forth in claim 2, wherein the locking protrusions on the upper and lower disc are arranged at angular positions offset with respect to each other.

6. The injection device as set forth in claim 2, wherein an ampoule holder comprises the lower disc or is coupled to it and is axially retracted towards the operating button against a restoring force of the second restoring element, such that the rotational grid locks.

7. The injection device as set forth in claim 6, wherein the second restorer is generally between a rear part of the injection device and the ampoule holder.

8. The injection device as set forth in claim 7, wherein a length of the ampoule and a length of a front part of the injection device are adjusted to each other, such that the rotational grid locks when the ampoule is inserted into the front part and the front and rear parts are connected to each other.

9. The injection device as set forth in claim 8, wherein the second restorer is a pressure spring which is not fully compressed when the front and rear parts are connected to each other.

10. The injection device as set forth in claim 9, wherein the restoring force of the second restorer is smaller than the restoring force of the first restorer.

11. The injection device as set forth in claim 2, wherein the activating means further comprises a guiding element for the driven member.

12. The injection device as set forth in claim 11, wherein the guiding element is fixedly connected to the rear part of the device and the driven member is mounted non-rotatably in the guiding element.

13. The injection device as set forth in claim 12, wherein the drive element is arranged between the operating button and the fixed guiding element.

14. The injection device as set forth in claim 12, wherein the fixed guiding element is arranged between the operating button and the drive element.

15. The injection device as set forth in claim 2, wherein the driven member which can be moved in the advancing direction of the piston is non-rotatable with respect to a casing of the device, and wherein by rotating the operating button in the resting position, the driven member spaced apart from the piston can be moved in the advancing direction by the drive element in accordance with a piston path required for the respective amount of product to be injected, and wherein the driven member remains spaced apart from the piston, and while the drive element is transferred from the resting position to the end position, the driven member comes to rest on the piston, in order to shift the piston by the thus pre-selected piston path.

16. The device as set forth in claim 2, further comprising a 30-gauge or 31-gauge injection needle.

17. The injection device as set forth in claim 1, wherein the locking bodies comprise recesses running in the axial direction of the injection device and correspondingly formed protrusions running in the axial direction are provided on the outer circumference of the operating button or the element arranged non-rotatably with respect to it.

18. The injection device as set forth in claim 17, wherein the locking bodies produce clicking sounds synchronously with the sounds produced by the locking protrusions sliding relative to the locking recesses such that angular positions of the locking bodies correspond substantially to the angular position of the locking protrusions and/or recesses of the rotational grid.

* * * * *